United States Patent [19]  
Hofmann et al.

[11] 3,936,490  
[45] Feb. 3, 1976

[54] PROCESS FOR CONDUCTING ORGANONITRILE ADDITION REACTIONS

[75] Inventors: John E. Hofmann, Alan Schriesheim, both of Berkeley Heights, N.J.

[73] Assignee: Exxon Research and Engineering Company, Linden, New Jersey

[22] Filed: Dec. 22, 1970

[21] Appl. No.: 100,811

Related U.S. Application Data

[63] Continuation-in-part of Ser. No. 460,508, June 1, 1965, Pat. No. 3,595,930.

[52] U.S. Cl....... 260/465.3; 260/465 R; 260/465 C; 260/465.8 R; 260/465.9; 260/540; 260/586 R; 260/593 R; 260/617 R; 260/668 F; 260/677 R
[51] Int. Cl.$^2$...................................... C07C 120/00
[58] Field of Search.......... 260/465.3, 465.9, 465 A, 260/465 K, 465 C, 465.8 R

[56] References Cited

UNITED STATES PATENTS

2,971,024    2/1961    Zaugg et al................. 260/465.4 X

OTHER PUBLICATIONS

Pearson, et al., J.A.C.S., 75 (1953), pp. 2439–2443.
Rappoport, *The Chemistry of the Cyano Group*, 1970, pp. 125–127.
Kosower, *Physical Organic Chemistry*, 1968, pp. 21–41.

*Primary Examiner*—Joseph P. Brust
*Attorney, Agent, or Firm*—Robert J. Baran

[57] ABSTRACT

Process for reacting organonitriles with hydrocarbon substrates, by contacting with a basic alkali metal catalyst in a solvent selected from the group consisting of trimethyl phosphoramide, hexamethyl phosphoramide, tetramethyl urea and N-methyl-2-pyrollidone.

10 Claims, No Drawings

PROCESS FOR CONDUCTING ORGANONITRILE ADDITION REACTIONS

CROSS REFERENCES TO RELATED APPLICATIONS

This is a continuation-in-part application Ser. No. 460,508, filed June 1, 1965, in the names of John E. Hofmann and Alan Schriesheim, now U.S. Pat. No. 3,595,930.

BACKGROUND OF THE INVENTION

1. Field of the Invention

The present invention pertains to a method for carrying out addition reactions and particularly to anionic addition and condensation reactions through the generation of hydrocarbon carbanions.

2. Description of the Prior Art

Theoretically, almost any anionic addition reaction could be carried out as long as a nucleophilic molecule and a substrate molecule are present. The present state of the art, however, limits reactions to materials containing specific functional groups. The Michaels condensation, for example, carried out in conventional solvents is limited to very acidic nucleophiles ($pK_a$'s of 10 – 25) and substrates such as $\alpha, \beta$ unsaturated ketones.

It is the object of this invention to provide a process which will greatly extend the type or types of compounds that will participate in addition or condensation type reactions.

It is also an object of this invention to provide a process whereby very weakly acidic materials may serve as nucleophiles in condensation or addition reactions.

It is a further object of this invention to provide a process whereby simple hydrocarbons may serve as substrates in condensation and addition reactions.

These and other objects will appear more clearly from the detailed specification which follows.

SUMMARY OF THE INVENTION

It has now been found that acidic materials, including weakly acidic materials having a $pK_a$ as high as about 35 will react as nucleophiles with simple hydrocarbons as substrates if the reaction is carried out in contact with a basic reagent in the presence of certain special solvents. Specifically, it has been found that nucleophilic molecules of the general formula $XCH_3$, wherein X is an active electron withdrawing group such as a nitro, nitrile, carbonyl, sulfoxy, sulfone, aryl or vinyl, will react with simple hydrocarbon substrates of the formula $R—CH=CH_2$ wherein R stands for an aryl or vinyl radical, preferably a simple hydrocarbon such as butadiene, when maintained in contact with a suitable base, preferably potassium tertiary butoxide, and alkyl phosphoramide solvents to produce a broad scope of materials ranging from lube oils to chemical specialties.

The base employed in the base-solvent system may be any of a wide variety of materials. The only limitation on this material is that it have sufficient basicity to permit the reactions to proceed at a satisfactory rate. Examples of suitable bases include alkali metal hydrides, such as sodium hydride, alkali metal organic amides such as sodium methyl amide; alkali metal amides as $NaNH_2$, alkali metal alkoxides such as sodium methoxide or ethoxide, potassium t-butoxide; alkali metal hydroxides such as sodium, potassium or cesium hydroxide and alkali metal alkyls such as sodium ethyl or butyl lithium. Particularly preferred are bases containing the heavy alkali metals, e.g. potassium, cesium and rubidium. Furthermore, where the base has an alkyl group, effectiveness is increased by increasing the number of carbon atoms. For Example, $KOC_2H_5$ is more effective than $KOCH_3$ and K-t-butylate is more effective than either of the foregoing. This listing is by way of illustration only since other suitable bases will readily occur to those skilled in the art.

The particular solvent used is of critical importance. Obviously, the solvents employed in the instant invention must be base stable, i.e. resistant to decomposition in the presence of the base and the reactants. Alkyl phosphoramides such as trimethyl phosphoramide and hexamethyl phosphoramide and tetraalkyl ureas such as tetramethyl area are unique in bringing about the desired condensation in a reasonable time while avoiding complicating side reactions. Another solvent which is effective within the scope of the instant invention is N-methyl-2-pyrollidone.

Suitable nucleophilic compounds of the general formula $XCH_3$ as defined above which may be condensed with hydrocarbon substrates in accordance with the present invention include acetonitrile, acrylonitrile, isobutyronitrile, acetaldehyde, isobutyraldehyde, acetone, diisopropylketone, aryl methanes such as toluene, diphenylmethane, di-p-tolylmethane, allyl benzene, and p-nitrotoluene. Preferably, the nucleophilic compounds have no more than about 40 carbon atoms in the molecule and include organonitriles such as n-valeronitrile, n-decanonitrile, 4-methylhexadecano-3-nitrile, cyclohexanonitrile, n-eicosanonitrile, 3-ethylhexaeicosanonitrile, etc.

The simple hydrocarbons which may be used as substrates for condensation with the above-mentioned nucleophilic reagents correspond to compounds having the following general formula:

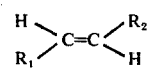

wherein $R_1$ is selected from the group consisting of hydrocarbyl radicals having the general formulas:

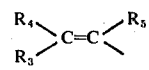

and

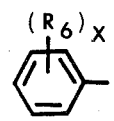

wherein $R_3$, $R_4$, $R_5$ and $R_6$ are selected from the group consisting of hydrogen, $C_1$ to $C_{10}$ alkyl, $C_5$ to $C_{10}$ cycloalkyl, $C_2$ to $C_{10}$ alkenyl, $C_6$ to $C_{10}$ aryl, $C_7$ to $C_{10}$ alkaryl, and $C_7$ to $C_{10}$ aralkyl radicals, and X is a positive integer of from 0–5 and represents the number of substituents present on the aromatic nucleus, and $R_2$ is selected from the group consisting of hydrogen and $C_1$ to $C_{10}$ alkyl radicals; and

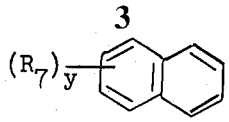

wherein $R_7$ is selected from the group consisting of hydrogen and $C_1$ to $C_{10}$ alkyl radicals and $y$ is a positive integer of from 0–7 and represents the number of substituents present on the aromatic nucleus. Preferably $R_2$, $R_3$, $R_4$, $R_5$, $R_6$, and $R_7$ are selected from the group consisting of hydrogen, methyl and ethyl radicals, and $X$ and $y$ are less than 2. Most preferably the hydrocarbon substrate is selected from the group consisting of butadiene, isoprene, piperylene, styrene, alpha methyl styrene and anthracene.

The reaction phase may be either homogeneous or heterogeneous depending upon the particular base-solvent system used. Where the base is soluble in the solvent, such as various alkoxides (potassium t-butoxide) then the reaction is homogeneous in base and may, if desired, be homogeneous in the hydrocarbon. Practically, the reaction could be operated heterogeneously where the feed and product are separated by a simple mixer-settler operation. Certain bases such as potassium hydroxide and sodium hydroxide, are insoluble and here a fixed bed might be used with the reactants and solvent contacting the base.

The particular ratios of solvent to base and base to reactants are dependent upon a variety of factors. For example, in homogeneous systems, it is desirable to have at least 1 wt. % of base dissolved in the solvent up to saturation. It is preferable that from about 3 to 10 wt. % of the base-solvent system be composed of base. In heterogeneous base-solvent systems, since the base is practically insoluble, the amount of solvent must be sufficient to ensure complete wetting of the surface of the base. More solvent may be used if it is desirable to dissolve the feed.

The ratio of the amount of base to the reactants should be about 1 mole of base to about 1 mole of nucleophile. Lower ratios are possible but generally undesirable because of the slowness in the rate and by the disastrous effect of trace quantities of hydroxylic-containing materials. Higher ratios could be used but would be uneconomic. The preferred range would be 0.5 to 3 moles of base per mole of nucleophile.

In carrying out the condensation in accordance with the present invention the temperature of the reaction mixture is maintained between about 10° and 100°C., preferably at about 25°C. The reaction is continued for a period of about 1 to about 20 hours.

The following examples are illustrative of the present invention.

The bulk of the experimental work which forms the basis of the following examples involved the use of 0.6 molar solutions of potassium tert-butoxide (KOtBu) in hexamethyl phosphoramide (HMPA) at room temperature. With acetonitrile several other media were tried. All solutions were prepared in a nitrogen dry box. For most of the reagents blank experiments were run to determine the extent of reaction in the absence of one or the other reagent. During the course of an experiment, small aliquots were analyzed periodically by gas chromatography to get any estimate of reaction rates. These rates were then compared on the basis of the first order rate of butadiene consumption. (This value is only qualitative since butadiene consumption is not exactly first order and is sometimes consumed by several reactive positions on the same molecule.) The final product was freed from the solvent by water dilution and analyzed by a combination of gas chromatography, mass spectrometry, infrared spectroscopy (IR) and nuclear magnetic resonance (NMR).

EXAMPLE 1

Acetonitrile was chosen for the initial process studies because it has fairly acidic hydrogens ($pK_a \sim 25$) and contains a functional group that can be converted to other useful intermediates. It is also capable of reacting in several different ways. Successive replacement of α-hydrogens would lead to mono, di and tri-butenylacetonitriles (reactions 1–3).

| | | |
|---|---|---|
| $CH_3CN + C_4H_6$ | $(C_4H_7)CH_2CN$ | (1) |
| $(C_4H_7)CH_2CN + C_4H_6$ | $(C_4H_7)_2CHCN$ | (2) |
| $(C_4H_7)_2CHCN + C_4H_6$ | $(C_4H_7)_3C\ CN$ | (3) |

On the other hand, the initial product might isomerize to an α,β unsaturated nitrile which could react with another molecule of acetonitrile (reactions 4 and 5).

(4)

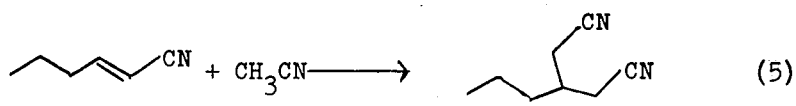
(5)

The exact mode of addition could most likely be controlled by the ratio of the reactants.

The reaction was studied using KOtBu in HMPA at butadiene to acetonitrile ratios ranging from 0.5 to 4. For each experiment, 3.25 g. of KOtBu was dissolved in 50 ml. of HMPA in a nitrogen purged drybox. The solution was placed in a 100 ml. Erlenmeyer flask and sealed with a puncturable serum cap. 2.0 g. of acetonitrile was added to each flask with a hypodermic syringe. From 1.45 to 11.6 g. of butadiene was then added via a hypodermic syringe needle from a sight glass containing a solution of 50 wt. % butadiene in n-heptane. Small aliquot samples were withdrawn periodically and analyzed by gas chromatography to determine the extent of reaction. At the conclusion of an experiment the entire mixture was quenched with 100 ml. of $H_2O$. The aqueous solution was then extracted several times with benzene and the resulting organic phase was analyzed by a combination of gas chromatography, mass spectrometry, infrared spectrometry and nuclear magnetic resonance.

The reaction proceeded rapidly at room temperature and in all cases was essentially complete in less than one hour. In all cases the selectivity to the trisubstituted nitrile was very high.

| Mole Ratios | | | | |
|---|---|---|---|---|
| $C_4H_6/CH_3CN$ | 0.54 | 1.03 | 1.95 | 4.1 |

-continued

| Conditions | 1 hour at RT | | | |
|---|---|---|---|---|
| Yield* Wt. % | 122 | 141 | 85 | 70 |
| Selectivities | | | | |
| $(C_4H_7)_3C\ CN$ | 84.0 | 92.7 | 92.9 | 97.3 |
| $C_{13}H_{20}$ | 3.5 | 1.4 | 2.6 | 2.0 |

*Wt. % on butadiene (theoretical at 3/1 = 125).

Minor amounts of other products were formed but never in sufficient quantity for positive identification. The failure of mole ratio to have any significant effect on selectivity indicates that the reaction becomes more rapid as substitution increases. This was confirmed during studies with isobutyronitrile in which 1.35 g. of the latter were reacted with 1.0 g. of butadiene in the presence of 3.25 g. KOtBu and 50 ml. HMPA at 25°C. for 2 hours. 2.2 g. of product, mainly dimethylbutenylacetonitrile, were recovered and the first order rate of butadiene disappearance was $>6.4 \times 10^{-4}$, a rate somewhat faster than the initial rate observed for acetonitrile.

The hydrocarbon product, $C_{13}H_{20}$, obtained with acetonitrile undoubtedly arises from elimination of HCN from the initial product. The amount of elimination is fairly small at one hour but increases markedly as reaction time increased.

| Time, Hrs. | 1.0 | 22.5 |
|---|---|---|
| $C_4H_6/CH_3CN$ | 1.95 | 1.75 |
| Yield, Wt. % | 85 | 120 |
| Selectivities | | |
| $(C_4H_7)_3C\ CN$ | 92.9 | 55.9 |
| $C_{13}H_{20}$ | 2.6 | 36.8 |

The elimination reaction was also studied by contacting a preformed nitrile product with KOtBu in HMPA at 55°C. At the end of 20 hours, it was found that only 39% of the initial nitrile remained. In general, the elimination reaction should be minimized because it consumes the catalyst, although the $C_{13}$ tetraolefin produced by elimination might have some interesting properties.

In order to minimize elimination and also to study the generality of the reaction, several other combinations of base and solvent tabulated below were tried.

| Solvent | HMPA | HMPA | HMPA + 4% t-BuOH | TMU |
|---|---|---|---|---|
| Base | KOtBu | KOH | KOtBu | KOtBu |
| Time, Hrs. | 1.0 | 5.0 | 5.0 | 5.0 |
| Rel. Rate | 1.0 | 0.025 | 0.063 | 0.04 |
| Yield, Wt. % | 85 | 84 | 83 | 44 |
| Selectivities | | | | |
| $(C_4H_7)_3C\ CN$ | 92.9 | 94.8 | 92.9 | 92.7 |
| $C_{13}H_{20}$ | 2.6 | 0.6 | 2.1 | 0.0 |

Potassium hydroxide, which is insoluble in HMPA, catalyzes the addition reaction but at a considerably reduced rate. There was slightly less elimination with KOH. When tert-butyl alcohol is added to HMPA the rate drops off markedly but there is essentially no change in selectivity. With TMU (tetramethylurea), a less active solvent as compared to HMPA, the reaction is also considerably slower but there is essentially no elimination.

The preceding data clearly show the ease with which the addition reactions are carried out in alkyl phosphoramide solvents. Although the reaction mechanism dictates that only one product can be formed in high yield, the reaction itself can be carried out at various conditions using different solvents and bases. The trisubstituted product might have several uses with one in particular being in the preparation of ester lubricants. Hydrolysis and hydrogenation should lead to a carboxylic acid which upon esterification with the corresponding alcohol will result in a highly hindered ester.

EXAMPLE 2

Isobutyronitrile is fairly similar to acetonitrile except that it has only one α-hydrogen. The reaction of this nitrile with butadiene was studied to evaluate a synthetic route to simple, highly hindered carboxylic acids. Isobutyronitrile reacts at a rate about 1.5 to 2 times faster than acetonitrile and the product consists of a mixture of double bond isomers of dimethylbutenylacetonitrile $(C_4H_7)C(CH_3)_2CN$. This product is formed with essentially 100% selectivity. Aqueous hydrolysis of this material resulted in a 90% yield of the corresponding unsaturated carboxylic acid which in turn was readily hydrogenated to α, α-dimethylhexanoic acid

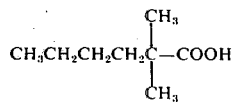

The hexanoic acid is very similar to acids presently employed for the synthesis of ester lubricants.

Data from two additional runs are summarized in the following table:

| Exp. Run | A | B |
|---|---|---|
| Temp., °C. | 25 | 25 |
| HMPA, ml. | 50 | 200 |
| Base | | |
| Type | KOtBu | KOtBu |
| Amt., g. | 3.25 | 14.0 |
| Reactant | | |
| Type | Isobutyronitrile | Isobutyronitrile |
| Amt., g. | 1.35 | 5.96 |
| mM. | 19.5 | 86.3 |
| Substrate | | |
| Type | Butadiene | Butadiene |
| Amt., g. | 1.0 | 6.0 |
| mM. | 18.3 | 111.0 |
| Time, Hrs. | 2.0 | 2.0 |
| Prod. Rec'd, g. | 2.2 | 8.0 |
| First Order Rate | | |
| of $C_{4==}$ disap.; sec.$^{-1}$ | $>6.4 \times 10^{-4}$ | — |
| Elemental, Wt. % | | |
| C | | 78.27 |
| H | | 10.37 |
| N | | 10.28 |
| O | | <.01 |
| P | | — |

When n-valeronitrile, n-decanonitrile, cyclohexanonitrile, n-eicosanonitrile, or 3-ethylhexaeicosanonitrile is substituted for isobutyronitrile in the experiment described in example 2(B), substantially identical results are obtained, in that a butadiene-organonitrile addition product is produced.

When isoprene, piperylene, styrene, α-methyl styrene or anthracene is substituted for butadiene in the experiment described in example 2(B), substantially identical results are obtained in that an addition product of the hydrocarbon and isobutyronitrile is produced.

When sodium hydride, sodium methyl amide, cesium hydroxide, or butyl lithium is substituted for potassium tertiary butoxide in the experiment described in example 2(B), substantially identical results are obtained in that the addition product of isobutyronitrile and butadiene is produced.

When N-methyl-2-pyrollidone or trimethyl phosphoramide is substituted for hexamethylphosphoramide in the experiment described in example 2(B) substantially identical results are obtained in that the addition product of isobutyronitrile and butadiene is produced.

either product can be achieved by varying the ratio of butadiene to the ketone.

The data from several additional runs are summarized in the following table.

| Exp. Run | 3A | 3B | 3C | 3D | 3E |
|---|---|---|---|---|---|
| Temp., °C. | 25 | 25 | 25 | 25 | 25 |
| HMPA, ml. | 200 | 50 | 50 | 50 | 50 |
| Base | | | | | |
| Type | KOtBu | KOtBu | KOtBu | KOtBu | KOtBu |
| Amt., g. | 14.0 | 3.25 | 3.25 | 3.25 | 3.25 |
| Reactant | | | | | |
| Type | Isobutyr-aldehyde | Isobutyr-aldehyde | Diisopropyl-ketone | Diisopropyl-ketone | Diisopropyl-ketone |
| Amt., g. | 5.96 | 1.44 | 2.28 | 1.51 | 2.79 |
| mM. | 82.8 | 20.0 | 20.0 | 13.3 | 24.5 |
| Substrate | | | | | |
| Type | Butadiene | Butadiene | Butadiene | Butadiene | Butadiene |
| Amt., g. | 6.0 | 1.0 | 1.0 | 2.0 | 0.74 |
| mM. | 111.0 | 18.3 | 18.3 | 36.6 | 13.7 |
| Time, Hrs. | 49.0 | 44.0 | 2.0 | 2.0 | 2.0 |
| Prod. Rec'd, g. | 8.2 | 1.53 | 2.64 | 2.3 | 2.5 |
| First Order Rate of $C_{4==}$ disap.; sec.$^{-1}$ | — | $4.5 \times 10^{-6}$ | $4.5 \times 10^{-4}$ | — | — |
| Elemental, Wt. % | | | | | |
| C | 75.78 | 75.30 | 79.11 | | |
| H | 10.89 | 11.77 | 11.93 | | |
| N | 0.04 | 0.17 | 0.10 | | |
| P | <.01 | 0.10 | 0.04 | | |
| O | 13.28 | 12.66 | 8.82 | | |

EXAMPLE 3

Isobutyraldehyde (IBA) and diisopropylketone (DIPK) were chosen as representative nucleophilic molecules containing the aldehyde and ketone group (carbonylic groups) because they contain a minimum of replaceable hydrogens. These materials are known to undergo base catalyzed auto-condensations (aldol condensations) but blank experiments in the absence of butadiene indicated only minor amounts of reaction. Data from three of the reactions of butadiene with DIPK are set out in the following table:

| Conditions | 2 hours at RT | | |
|---|---|---|---|
| $C_4H_6$/DIPK, Mole Ratio | 0.56 | 0.92 | 2.75 |
| Yield, Wt. %* | 340 | 260 | 115 |
| Selectivities | | | |
| Mono | 93 | 72 | 18 |
| Mixed** | 7 | 8 | 11 |
| Di | — | 20 | 64 |

\* Wt. % on butadiene, theoretical at 1/1 = 367 wt. %
\*\* Absolute amount of mono- and di-adducts in this fraction is unknown DIPK reacted rapidly with butadiene, at a relative rate of 0.5 compared to acetonitrile, and produced both mono and di addition products according to equations A and B.

$(CH_3)_2CHCOCH(CH_3)_2$ +
$C_4H_6 \rightarrow (CH_3)_2C(C_4H_7)COCH(CH_3)_2$ (A)
$(CH_3)_2C(C_4H_7)COCH(CH_3)_2 + C_4H_6$
$\rightarrow [(CH_3)_2C(C_4H_7)]_2 CO$ (B)

In this case the first reaction has very little effect on the rate of the second reaction and high selectivities to either product can be achieved by varying the ratio of butadiene to the ketone.

The reaction of isobutyraldehyde with butadiene was found to be unique among the anionic addition reactions studied. The reaction is fairly slow and 44 hours were required to get an appreciable yield. Mass spectrometry indicated the presence of both low and high molecular weight products. A detailed study of the low M.W. product by NMR proved the structure to be 4,4-dimethyl-5-hydroxycyclohexene. This undoubtedly arises via an intramolecular addition to the carbonyl following the initial reaction (reaction C).

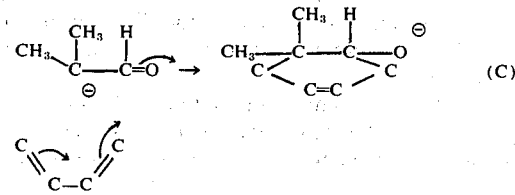
(C)

Overall, the yield of 4,4-dimethyl-5-hydroxycyclohexene was about 40% of theoretical. This material, once formed, can then undergo base catalyzed isomerization to yield a cyclohexanone (reaction D).

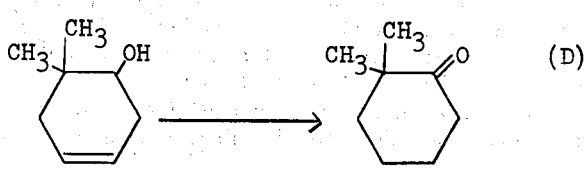
(D)

The cyclohexanone has reactive α-hydrogens and thus could be the source of higher molecular weight products. No ketone was found in the lower molecular weight region so the ketone formed in reaction (D) must be more reactive than the initial isobutyraldehyde. Subsequent work with cyclohexanone proved this to be the case. The intramolecular cyclization is a novel reaction and provides a new technique for synthesis of $C_6$ rings.

EXAMPLE 4

The benzylic hydrogens on alkyl aromatics represent the most weakly acidic materials of all those studied ($pK_a$'s of 33–38). Diaryl methanes and allyl benzene react fairly rapidly with butadiene while toluene reacted only very slowly. Diphenylmethane and di-p-tolylmethane reacted with butadiene at rates relative to acetonitrile of 0.5 and 0.05, respectively. The inhibition of rate by p-methyl groups is consistent with hydrocarbon acidity data. The products from both diaryl methanes include mono and disubstituted methanes (reactions E and F).

$$(R-\phi)_2CH_2 + C_4H_6 \rightarrow (R-\phi)_2CHC_4H_7 \quad (E)$$
$$(R-\phi)_2CHC_4H_7 + C_4H_6 \rightarrow (R-\phi)_2C(C_4H_7)_2 \quad (F)$$

Upon hydrogenation the disubstituted methanes, particularly from the di-p-tolylmethane, should make excellent lubes.

The products from the reaction of allyl benzene appear to be rather complex and consist of mixtures of multisubstituted allyl benzenes with addition occurring at both the alpha and gamma carbon atoms on the side chains. Toluene did not yield enough product for further study.

Data are summarized in the following table.

| Exp., 1037- | 39 | 113 | 40 | 114 |
|---|---|---|---|---|
| Temp., °C. | 25 | 25 | 25 | 25 |
| HMPA, ml. | 200 | 50 | 200 | 50 |
| Base | | | | |
| Type | KOtBu | KOtBu | KOtBu | KOtBu |
| Amt., g. | 13.0 | 3.25 | 13.0 | 3.25 |
| Reactant | | | | |
| Type | Diphenyl-methane | Diphenyl-methane | Di-p-tolyl-methane | Toluene |
| Amt., G. | 20.0 | 3.36 | 24.0 | 1.62 |
| mM. | 119 | 20.0 | 122 | 16.5 |
| Substrate | | | | |
| Type | Butadiene | Butadiene | Butadiene | Butadiene |
| Amt., g. | 12.15 | 1.31 | 12.15 | 1.31 |
| mM. | 225 | 24.3 | 225 | 24.3 |
| Time, Hrs. | 21.0 | 21.0 | 51.0 | 21.0 |
| Prod. Rec'd, g. | 32.2 | 3.6 | 31.5 | 0.19 |
| First Order Rate of $C_4^{==}$ disap.; sec.$^{-1}$ | $2.1 \times 10^{-4}$ | $5.6 \times 10^{-4}$ | $6.0 \times 10^{-5}$ | |
| | | 91.00 | | |
| | | 8.20 | | |
| | | 0.39 | | |
| | | 0.24 | | |

EXAMPLE 5

Cyclopentanone and cyclohexanone were reacted with butadiene in accordance with the procedure of Example 1. The conditions and the yields are summarized in the following table:

| Exp., 1037- | 30 | 31 |
|---|---|---|
| Temp., °C. | 25 | 25 |
| HMPA, ml. | 50 | 50 |
| Base | | |
| Type | KOtBu | KOtBu |
| Amt., g. | 3.25 | 3.25 |

-continued

| Exp., 1037- | 30 | 31 |
|---|---|---|
| Reactant | | |
| Type | Cyclopentanone | Cyclohexanone |
| Amt., g. | 2.18 | 2.46 |
| mM. | 25.9 | 25.1 |
| Substrate | | |
| Type | Butadiene | Butadiene |
| Amt., g. | 1.5 | 1.5 |
| mM. | 27.7 | 27.7 |
| Time, Hrs. | 4.0 | 4.0 |
| Prod. Rec'd, g. | 1.7 | 2.2 |
| First Order Rate of $C_4^{==}$ disap.; sec.$^{-1}$ | $1 \times 10^{-4}$ | $4.5 \times 10^{-5}$ |

EXAMPLE 6

In order to demonstrate the use of substrates other than butadiene, acetonitrile has been added to anthracene in accordance with the procedure of Example 1. The conditions and yield are summarized in the following table.

| | |
|---|---|
| Temp., °C. | 25 |
| HMPA, ml. | 50 |
| KOtBu, g. | 3.25 |
| Anthracene, g. | 4.4 |
| Acetonitrile, g. | 1.0 |
| Time, Hrs. | 15 |
| Reaction Product | |
| 9-Methylanthracene, g. | 2.17 |
| 9,10-Dimethylanthracene, g. | 0.24 |

In this case the major product proves to be that derived from addition followed by subsequent elimination of HCN as per the following equations:

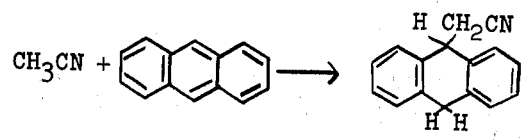

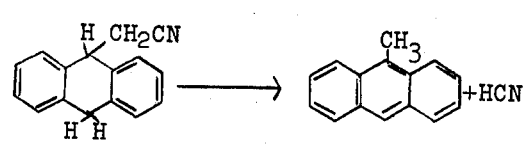

As indicated previously in Example 1, the amount of elimination could be controlled by variations in time, temperature, base and solvent.

The data that have been obtained have covered a fairly broad range of acidities. With this information, it is possible to construct the following very qualitative plot of reaction rates versus acidity (expressed as $pK_a$).

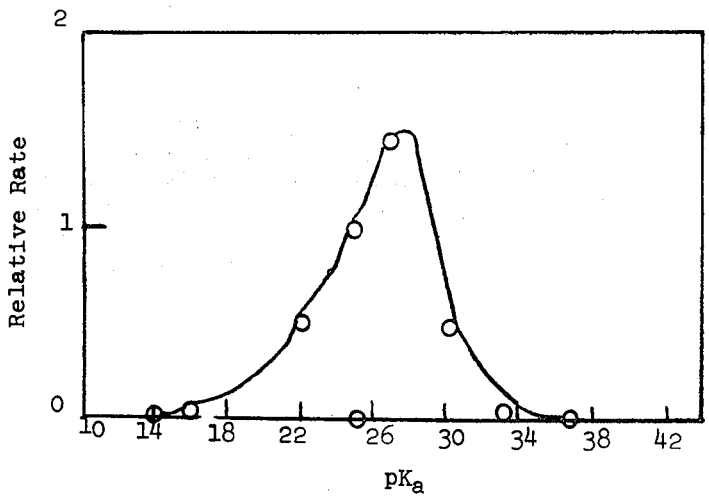

The plot is only qualitative because rate measurements are not very good and $pK_a$'s are not known very accurately. The data show a maximum rate at a $pK_a$ of about 28. It can be inferred that to the right of this point the ionization of the acidic reagent will be rate determining while to the left the addition reaction itself is rate determining. The $pK_a$ of acetonitrile starts at 25 and becomes higher as substitution increases thus accounting for the increase in reaction rate. Overall, these data indicate that appreciable reaction rates will be obtained with compounds having $pK_a$'s anywhere between 18 and 34, and preferably between about 22 and about 30.

The foregoing description contains a limited number of embodiments of the present invention. It will be understood that this invention is not limited thereto, since numerous variations are possible without departing from the scope of this invention as defined in the following claims.

What is claimed is:

1. A process for preparing a tri substituted nitrile which comprises reacting acetonitrile with butadiene, at a temperature of from about 10° to 100°C for a period of from about 1 to 25 hours, in the presence of a basic alkali metal catalyst, said catalyst being selected from the group consisting of alkali metal hydrides, alkali metal organo amides, alkali metal alkoxides, alkali metal hydroxides, and alkali metal alkyls, said reaction taking place in a solvent selected from the group consisting of trimethyl phosphoramide, hexamethyl phosphoramide, tetramethyl urea, and N-methyl-2-pyrollidone.

2. The process of claim 1 wherein said solvent is selected from the group consisting of hexamethyl phosphoramide and tetramethyl urea.

3. A process for preparing dimethyl butenyl acetonitrile which comprises reacting isobutyronitrile with butadiene at a temperature of from about 10° to 100°C for a period of from 1 to 25 hours in the presence of a basic alkali metal catalyst, said catalyst being selected from the group consisting of alkali metal hydrides, alkali metal organo amides, alkali metal alkoxides, alkali metal hydroxides, and alkali metal alkyls, said reaction taking place in a solvent selected from the group consisting of trimethyl phosphoramide, hexamethyl phosphoramide, tetramethyl urea, and N-methyl-2-pyrollidone.

4. The process of claim 3 wherein said basic alkali metal catalyst is selected from the group consisting of sodium hydride, sodium methylamide, sodium methoxide, sodium ethoxide, potassium-t-butoxide, sodium hydroxide, potassium hydroxide, cesium hydroxide, sodium ethyl and butyl lithium.

5. In the process of claim 3 wherein said solvent is hexamethylphosphoramide.

6. The process of claim 5 wherein said catalyst is potassium-t-butoxide.

7. The process of claim 1 wherein said catalyst is potassium-t-butoxide.

8. The process of claim 1 wherein the solvent is selected from the group consisting of trimethyl phosphoramide, hexamethyl phosphoramide, and tetramethyl urea.

9. The process of claim 1 wherein said basic alkali metal catalyst is selected from the group consisting of sodium hydride, sodium methylamide, sodium methoxide, sodium ethoxide, potassium-t-butoxide, sodium hydroxide, potassium hydroxide, cesium hydroxide, sodium ethyl and butyl lithium.

10. The process of claim 1 wherein said basic alkali metal catalyst is potassium tertiary butoxide.

* * * * *